United States Patent [19]

Capron et al.

[11] Patent Number: 5,071,959
[45] Date of Patent: Dec. 10, 1991

[54] NOVEL LYMPHOKINE FOR SUPPRESSING PLATELET ACTIVATION

[76] Inventors: André Capron, Phalempin; Michel Joseph; Véronique Pancre, both of Lille; Claude Auriault, Mouchin, all of France

[73] Assignee: Institut Pasteur de Lille, Lille; Institut National de la Sante et de la Recherche Medicale-INSERM, Paris, both of France

[21] Appl. No.: 168,009
[22] PCT Filed: May 19, 1987
[86] PCT No.: PCT/FR87/00164
§ 371 Date: Mar. 1, 1988
§ 102(e) Date: Mar. 1, 1988
[87] PCT Pub. No.: WO87/07303
PCT Pub. Date: Dec. 3, 1987

[30] Foreign Application Priority Data

May 21, 1986 [FR] France .................. 86 07194

[51] Int. Cl.$^5$ ............... C07K 15/00; C07K 15/02; C07K 3/20; C07K 3/28
[52] U.S. Cl. ............................ 530/351; 530/413; 530/417; 424/85.1
[58] Field of Search ............ 530/351, 412, 413, 417; 424/85.1

[56] References Cited

FOREIGN PATENT DOCUMENTS

85/00750 2/1985 World Int. Prop. O. .

OTHER PUBLICATIONS

Takakuma et al., J. of Immunol. 120(2), pp. 481–486, (1978).
Aggarwal, "Micropurification of Cytokines" in Protein Purification: Microtomacro, Burgess, ed., Alan R. Liss, Inc. (New York) 1987.
The Journal of Immunology, vol. 118, No. 6, Jun. 1977, The Williams & Wilkins Co. (Baltimore), U.S.), H.G. Remold et al., "Two Migration Inhibitory Factors With Different Chromatographic Behavior and Isoelectric Points", pp. 2015-2019.
The Journal of Immunology, vol. 131, No. 6, Dec. 1983, The Williams & Wilkins Co. (Baltimore, U.S.) T. M. Aune et al, "Purification and Initial Characterization of the Lymphokine Soluble Immune Response Suppressor", pp. 2848-2852, p. 2848 Abstract, rt-hand col., ¶ 4 & 5. p. 2849 left-hand column ¶ 1 & 2.
Nature, vol. 303, 30-Jun.-1983, Macmillan Journals Ltd (Chesham, Bucks, GB), M. Joseph et al.: "A New Function for Platelets IgE–Dependent Killing of Schistosomes", pp. 810-812, see the whole document (cited in the application).

Primary Examiner—Margaret Moskowitz
Assistant Examiner—Shelly J. Guest
Attorney, Agent, or Firm—Oblon, Spivak, McClelland, Maier & Neustadt

[57] ABSTRACT

New lymphokine and its isolation and purification process. Said lymphokine is comprised of a factor obtained from T cells stimulated by concanavaline A or by an antigen capable of inhibiting the IgE-dependent platelet citotoxicity with respect to young larvae of S. Mansoni, of strongly reducing the chemiluminescence of blood platelets in a reaction IgE-anti-IgE, which is a correlate of the anti-parasite cytotoxicity, and of inhibiting the platelet activation in non-IgE dependent intolerences. Application as suppressor agent for suppressing platelet activation and as immunomodulator medicament of allergies.

10 Claims, 4 Drawing Sheets

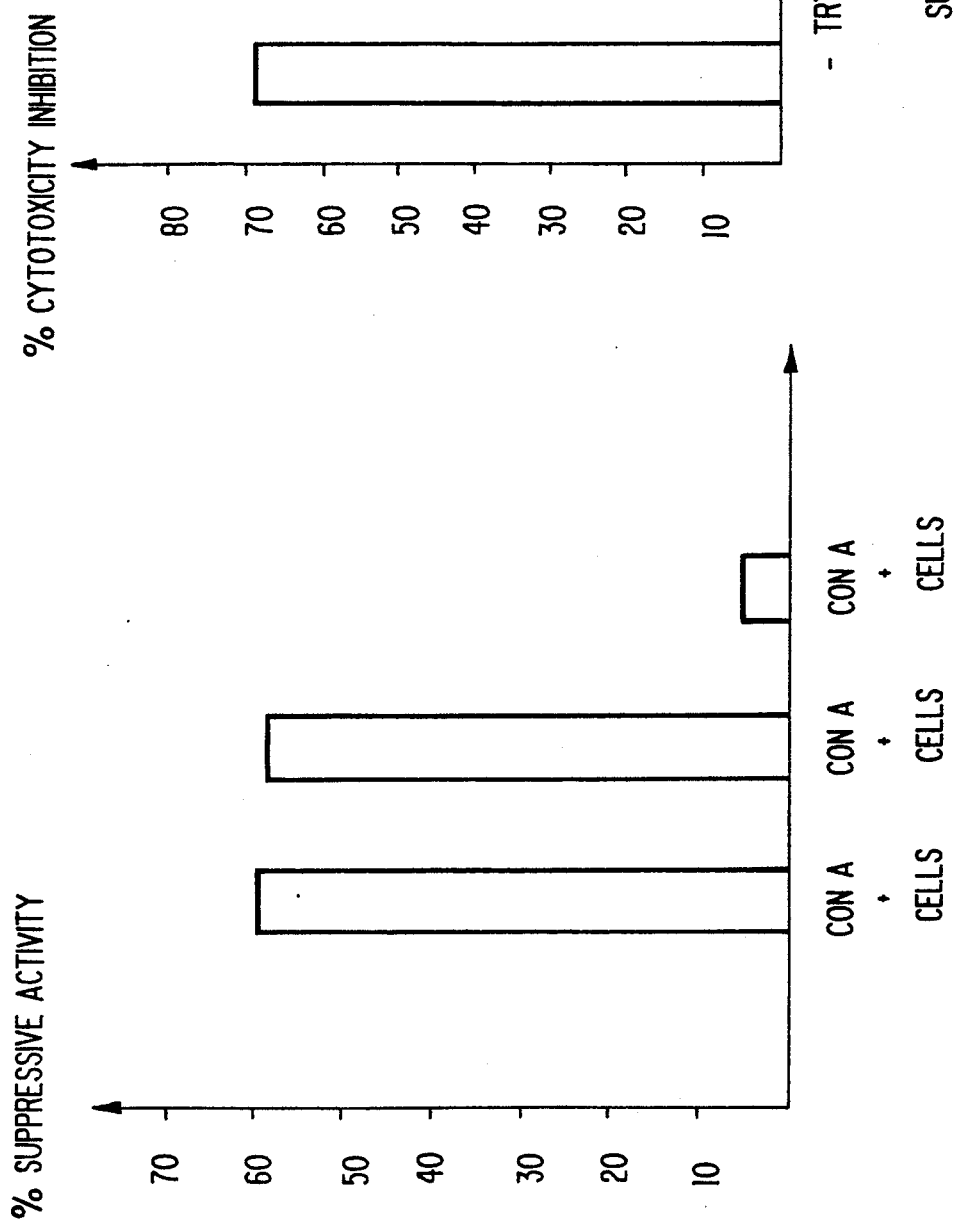

1

NOVEL LYMPHOKINE FOR SUPPRESSING PLATELET ACTIVATION

BACKGROUND OF THE INVENTION

The present invention relates to a novel lymphokine which suppresses platelet activation, to its process of isolation and purification and to medicaments containing it.

It is known that stimulated T cells excrete a certain number of soluble factors among which certain are capable of regulating the functions of effector cells.

It has been demonstrated recently (cf. M. JOSEPH, C. AURIAULT, A. CAPRON, M. VORNG and P. VIENS, NATURE 303:8IO) that blood platelets taken up in rats infected with Schistosoma mansoni, express antiparasite properties destructive in vitro, which increase in the course of the infection. The maximum cytoxicity has been observed when the rats have expressed a high level of immunity with respect to reinfection. This platelet cytoxicity declines rapidly after eight weeks of infection, despite the presence of IgE antibodies in the serum of these infected rats. This is the reason why the inventors have been led to consider that the factors of the T cells, produced after stimulation of suppressor T cells by circulating antigens of S. mansoni, play a role in this diminution, and this mechanism can appear as a regulation in return of immune functions of the platelets in the infection of the rat. In the same way, it has been shown that human platelets can be induced in cytoxic effectors against schistosomules, by incubation with serum rich in IgE of patients afflicted with schistosomiasis or asthmatic allergy patients, the cytoxic process being retarded in the latter case by the addition of anti-IgE or of a specific allergen (cf. M. JOSEPH, J. C. AMEISEN, J. P. KUSNIERZ, V. PANCRE, M. CAPRON and A. CAPRON, 1984, C. R. ACAD. SC. PARIS 298:55).

It is an object of the present invention to isolate a suppressor factor of the activity of the blood platelets, which is capable of playing, among other things, an immunomodulator role of allergic manifestations.

The present invention relates to a factor obtained from T cells stimulated by Concanavaline A or by an antigen, which can inhibit the IgE-dependant platelet cytotoxicity with respect to young larvae of S. mansoni, of greatly diminishing the chemoluminescence of platelets in an IgE-anti/IgE reaction, which is in correlation with the antiparasitic cytotoxicity and of inhibiting platelet activation in non-IgE dependant intolerances, which factor is denoted by the name of lymphokine for the suppression of platelet activation (LSPA) and is produced by T OKT8+ lymphocytes.

BRIEF DESCRIPTION OF THE DRAWINGS

FIG. 5 illustrates the level of respective suppressor activity of the LSPA obtained from T cells, from OKT8+ OKT4− cells and from OKT8− OKT4+ cells, stimulated by Concanavaline A.

FIG. 6 illustrates the percentage inhibition of the cytotoxicity of supernatants treated by trypsin, protease K and neuraminidase.

DETAILED DESCRIPTION OF THE PREFERRED EMBODIMENTS

Figure 1:
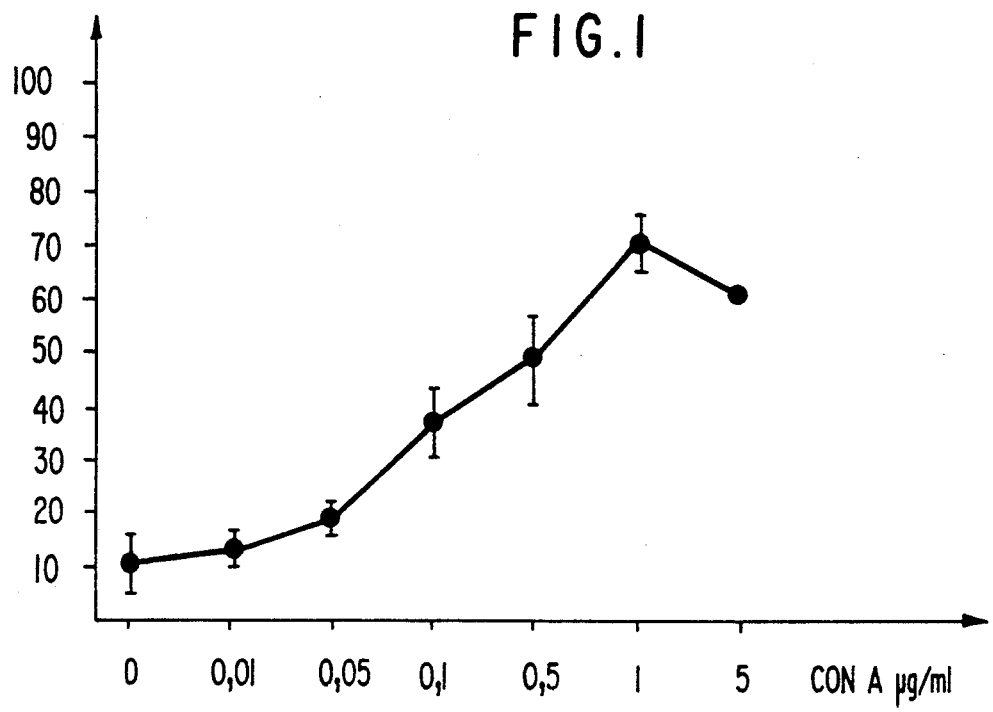
FIG. 1 shows the percentage inhibition of the cytotoxicity as a function of the amount of Concanavaline A used as a stimulant.

In one embodiment of LSPA, the latter is isolated from supernatants T OKT8 lymphocyte cultures stimulated by Concanavaline A or an antigen.

In another embodiment of LSPA, in the case where it is isolated from supernatants of T OKT8+ lymphocyte cultures stimulated by an antigen, the T lymphocytes have been stimulated by Echinococcus granulosus or Schistosoma mansoni antigens. The present invention also relates to a process of preparation of LSPA which consists of stimumlating T cells of human or murine origin with Concanavaline A or of a similar mitogenic stimulant or by an antigen taken from the group which comprises antigens of S. mansoni and antigens of Echinococcus granulosus, cultivating the stimulated T cells, for a suitable period, recovering the culture supernatants and filtering them, if necessary after centrifugation, through membranes of pore dimension of the order of 0.22 μm, then purifying them by gel filtration and subjecting the active protein fraction collected, previously identified by research of the biological or immunological activity and if necessary freeze-dried, to reverse phase chromatography on bonded silica gel, of calibrated granulometry and porosity, followed by elution by a gradient of $CH_3CN$—$H_2O$ containing 1% of trifluoroacetic acid, ranging from 1-99 to 60-40, the purified protein fraction containing the LSPA being then advantageously freeze-dried after detection by recording optical density at 215 nm and determination of the biological activity.

In an advantageous embodiment of the process for preparing the LSPA according to the present invention, the biological activity of the active protein fraction and of the purified active protein fraction containing the LSPA is determined by obtaining 60% inhibition of the cytotoxicity by the culture supernatant of T lymphocytes stimulated by Concanavaline A or by antigens of E granulosis, with respect to normal blood platelets used as effector cells, incubated with serum of patients afflicted with schistosomiasis or with serum of allergic patients having a high level of circulating IgE and stimulated by anti-IgE or by the specific allergen.

It is also an object of the present invention to provide a novel medicament for immunomodulating allergic manifestations which is characterized in that its active constituent is LSPA isolated from culture supernatants of T lymphocytes stimulated by a mitogenic agent such as Concanavaline A or the like or by a suitable antigen such as particularly an E granulosis or S mansoni antigen, which has the properties mentioned above and whose molecular weight is of the order of 15-20 kDa and Pi of the order of 4.4 to 5.0, which lymphokine possesses a specific linkage structure of the type of a receptor, at the surface of the blood platelets, that is to say a specificity of adsorption on the platelets.

The tests carried out to check the biological activity of the culture supernatant of T lymphocytes stimulated according to the present invention have permitted arrival at the following conclusions:

Effect of the supernatant on the cytotoxicity of the platelets

The supernatants obtained after the stimulation of normal human, peripheral or amygdal T lymphocytes, by Concanavaline A (0.01 at 5 µg/ml ) or T lymphocytes of the spleen of a patient afflicted with Echinococcosis, by E granulosis antigens (5 to 100 µg/ml), tested in cytotoxic processes of platelets with respect to schistosomules, have permitted results collected in the following Table 1 to be obtained:

TABLE I

Effect of the LSPA on the IgE dependant anti parasitic cytotoxicity of murine and human blood platelets derived from infected and allergic individuals

| Cytoxicity | Man [a] | | Rat [b] |
|---|---|---|---|
| | A | B | |
| In an activator medium | 72.7 ± 2.9 | 81.7 ± 5.5 | 71.2 ± 5.2 |
| with Con A supernatant | 20.5 ± 2.1 | 22.1 ± 4.0 | 19.5 ± 2.5 |
| with AG supernatant | 35.0 ± 15.0 | 33.6 ± 6.1 | 21.5 ± 0.5 |
| with lymphocyte culture | 70.2 ± 3.2 | 81.5 ± 4.6 | 78.0 ± 7.0 |

N.B. In all cases the cytotoxicity with normal human or rat serums, does not exceed 9.5 ± 7.3 a) The purified platelets were incubated with A serum (of patients afflicted with Schistosomiasis mansoni) or B (of allergic donors) in the presence of larvae of S mansoni (Schistosomules). The supernatant of lymphocytes or culture media of lymphocytes and anti-IgE's or corresponding allergen in the case of incubation in serum of allergic donors, were added and the cytotoxicity was evaluated as a percentage of schistosomules dead after a period of incubation of 24 hours at 37° C. (mean±standard deviation).

b) The purified platelets were incubated with serum of rats afflicted with Schistomiasis mansoni in the presence of larvae of S.mansoni (schistosomules). The supernatant of lymphocytes or the culture medium of lymphocytes was added and the cytotoxicity was evaluated as a percentage of schistosomules dead after a period of incubation of 24 hours at 37° C. (mean±standard deviation).

The Inventors have established that the supernatants are active directly on the platelet functions and not by protection of the targets, since the separate preincubation of the effector platelets or of the schistosomules with the supernatants of T lymphocytes, followed by a cytotoxicity test in which the platelets and the parasites have been separated by a membrane of polycarbonate of porosity 0.2 only ends the expected inhibition in the case where the platelets have been preincubated and not in the case where the larvae have been incubated, as emerges from Table 2 below:

TABLE 2

| Direct action of the LSPA on the human blood platelets | | | |
|---|---|---|---|
| | P/S | P*/S | P/S* |
| Cytoxicity IgE/anti-IgE | 92.3 ± 5.1 | 14.6 ± 9.2 | 71.5 ± 6.3 |

The human platelets (P) and the schistosomules (S), treated (*) or not by a supernatant of lymphocytes, have been separated by a filter (/) of polycarbonate of porosity 0.22 µm in Boyden chambers.

The cytotoxicity was evaluated as a percentage of schistosomules dead at the end of an incubation period of 24 hours at 37° C. (mean I.S.D.).

Moreover, the Inventors have demonstrated that this inhibition is not the consequence of a toxic effect of a supernatant of T lymphocytes since LDH has not been detected in the platelet suspension (Lactico-dehydrogenase).

Mitogenic stimulation of T lymphocytes of spleen of rats either by Concanavaline A or by PHA ((2 µg/ml); PHA=Phytohemagglutinin) or the antigenic stimulation of mesenteric T lymphocytes or of rat spleen infected with S. mansoni, by the antigen of adult schistosoma produced from supernatants which inhibit the IgE-dependent cytotoxicity of platelets of rats (40 to 60% inhibition), which shows that the T lymphocytes of rats secrete, in the same way as human T lymphocytes, LAPS lymphokine, which is a platelet inhibitor factor.

As is seen in the accompanying FIG. 1, which represents the percentage inhibition of the cytotoxicity as a function of the amount of Concanavaline A (expressed in µg/ml) used as a stimulant, the inhibitor effect is proportional to the dose of Concanavaline A used for the stimulation of T cells and the optimal effect is obtained at a final dose of 1 µg/ml. The supernatants produced in the absence of Concanavaline A also express a suppressive activity, but substantially less than that observed with supernatants activated with lectine (20-25%).

Figure 2:
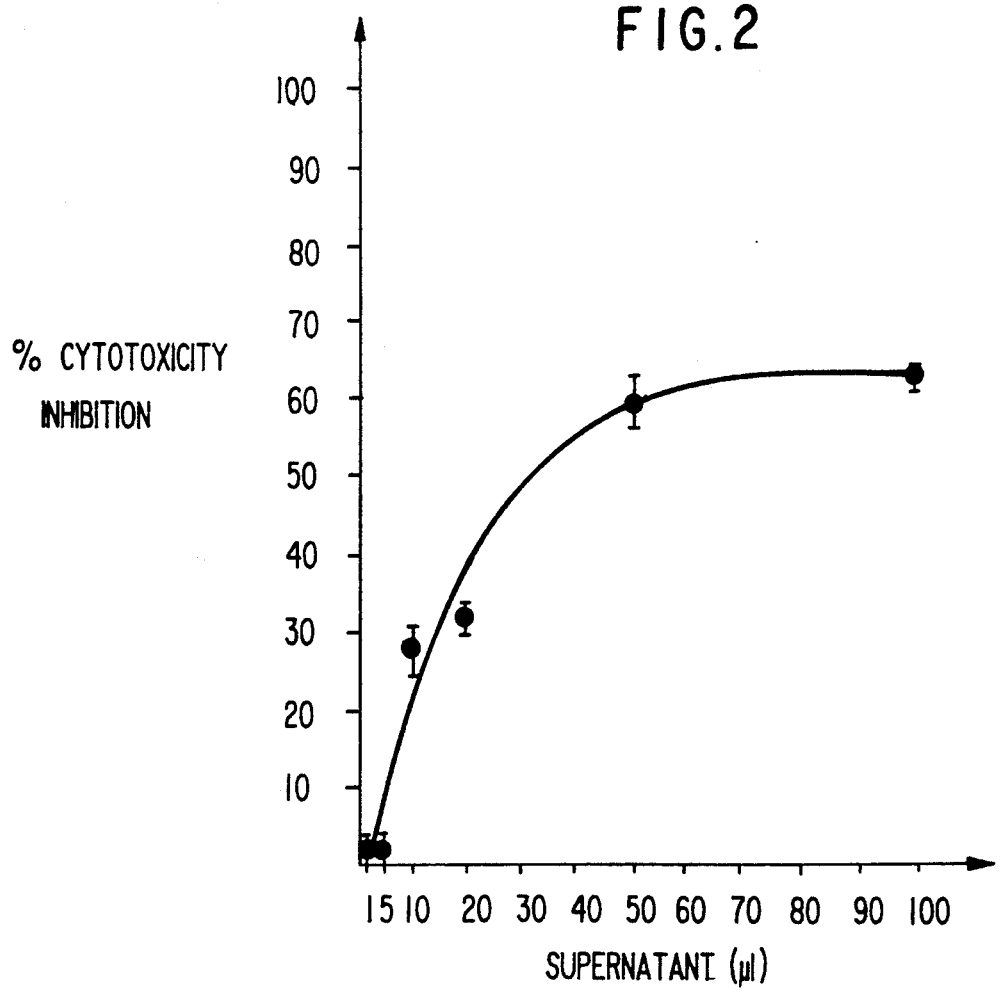
FIG. 2 shows the percentage inhibition of the cytotoxicity as a function of the amount of supernatant employed.
Figure 3:
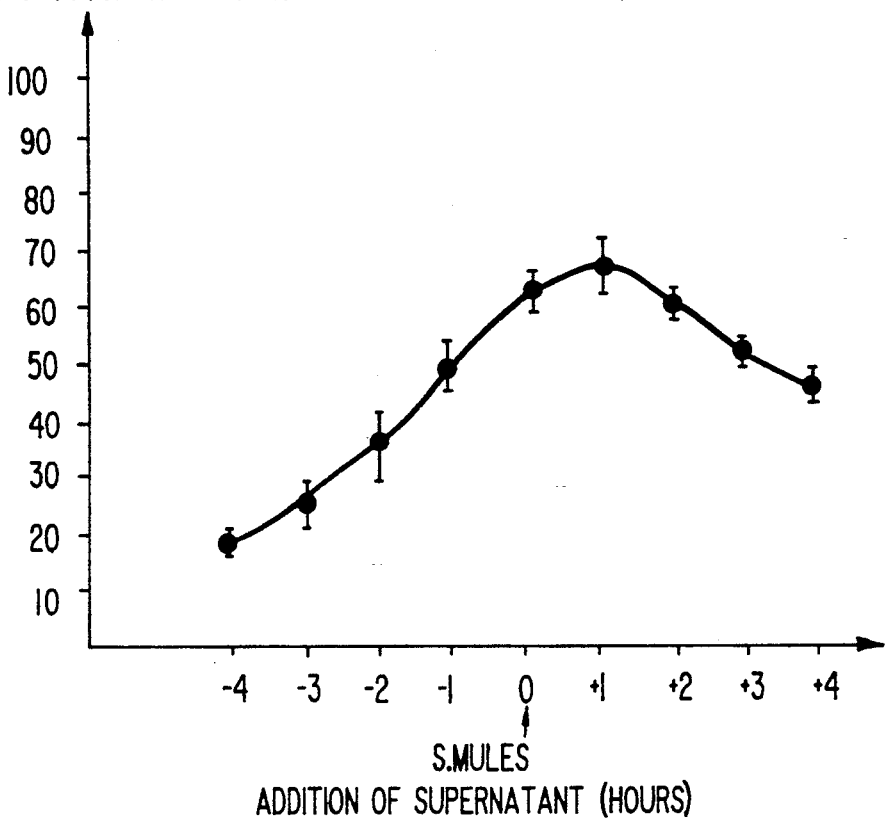
FIG. 3 shows the percentage inhibition of the cytotoxicity represented as a function of the addition of supernatant in time, expressed in hours.

As is seen in FIG. 2, which shows the percentage inhibition of the cytotoxicity as a function of the amount of supernatants (expressed in µl) employed, the supernatant acts in a manner which is the function of the amount employed to to reach a plateau at 50 µl (1:4 of final dilution), which is the dose used for all subsequent experiments. The effect of the addition of supernatants at different periods before and after the commencement of the cytotoxic process is shown in FIG. 3 attached in which the percentage inhibition of the cytotoxicity is represented as a function of the addition of supernatant in time, expressed in hours; the optimal inhibition has been obtained by the addition of T cell supernatant in the course of the first hours of contact between the effectual platelets and the schistosomules (in this figure "Smules" indicates schistosomules);

Structure of linkage to the platelets

Three successive incubations of supernatant of T cells which contain the factor according to the invention, which is capable of inhibiting the destructive properties of the platelets with respect to schistosomules, with platelets put into tablets, eliminate its inhibitor activity from the cytotoxicity of the platelets: this absorption of the suppressor factor by the platelets suggests the existence of a liaison structure. On the other hand, when there are used cell lines of IgE myeloma, of K562, of U937 or of broncho-alveolar macrophages as absorbants, the inhibitor effect of the supernatant of lymphocytes is preserved.

Effect of the supernatant on the chemoluminescence of the platelets

The Inventors have demonstrated previously (C.R. ACAD. SC. PARIS, 1984, 298:55 already mentioned) that, in the IgE-dependent toxicity relative to schistosomules, it is possible to obtain the production of metabolites of oxygen by human platelets, measured by chemoluminescence.

Figure 4:
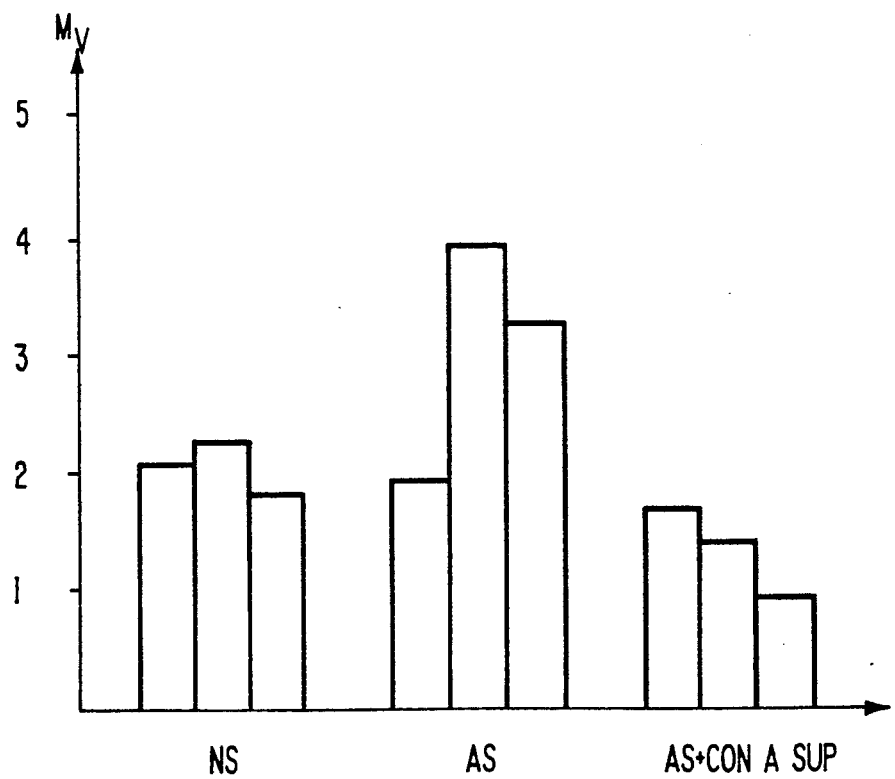
FIG. 4 shows the effect of the supernatant of T lymphocytes stimulated by Concanavaline A on the chemoluminescence of platelets.

The effect of the supernatent of T lymphocytes stimulated by Concanavaline A (1 μg/ml) on the chemoluminescence of the platelets has been tested: as shown by accompanying FIG. 4, incubation of platelets with lymphocyte T supernatant for one hour, at a final dilution of 1:4, considerably reduces (by 60%) the production of metabolites of oxygen which is normally observed in the case where the normal platelets have been stimulated by an IgE/anti-IgE reaction or in the case where the platelets of allergic patients have been stimulated by the corresponding allergen, which confirms the direct role of the lymphokine according to the invention, relative to the platelets themselves.

In FIG. 4, the initials NS and AS have the following meanings:
NS=incubated in normal serum,
AS=incubated in the serum of allegic patients,
AS+ConA Sup=incubated in the serum of allergic patients and the supernatant of lymphocytes.

The maximum activity of the luminol/luciferin chemoluminescence of $5.10^5$ platelets in PBS has been recorded in the five minutes which followed the addition of the medium (1st column of each group) or of the retarding agent: anti-IgE (10 μg of antibody/ml) (2nd column of each group) or allergen (10 μg/ml) (3rd column of each group).

Characterization of the cells involved in the production of suppressor lymphokine To define the type cell responsible for the production of the inhibitor factor according to the present invention, the Inventors have examined the effect of a depletion of the selective T subpopulation: they treated T cells with monoclonal OKT4 antibodies (for the auxiliary/inductor subclasses) or by OKT8 monoclonal antibody (for the suppressor/destructor subclasses) in the presence of complement. The cells were then stimulated by Concanavaline A and it was examined whether the suppressor lymphokine was produced.

As shown by FIG. 5, the depletion of OKT8+ lymphocytes suppressed the production of inhibitor factor, whilst the depletion of OKT4+ cells did not modify its formation. FIG. 5 illustrates the level of respective suppressor activity of the LSPA obtained from T cells, from OKT8+ OKT4− cells and from OKT8− OKT4+ cells, stimulated by Concanavaline A. The results are expressed in % suppression (mean) of the IgE-dependent cytotoxicity, with respect to schistosomules.

This observation shows indeed that a sub-population of suppressive T cells produces the factor responsible for the inhibition observed of the effector functions of the platelets.

Effect of the treatment of T cells with indomethacine on the production of inhibitor lymphokine (LSPA) according to the invention The prostaglandins play, as is known, a role in the induction of nonspecific suppressive T cells, during the mitogenic and antigenic stimulation of lymphocytes. The Inventors have therefore treated the lymphocytes with indomethacine ($10^{-5}$M final concentration) which is an inhibitor of the synthesis of protaglandins and they have examined the production of inhibitor lymphokine induced by the mitogenic agent. The production of this factor remained unchanged under these conditions (48.0±3.0% of suppressive activity with indomethacine, for 45.0±2.5% without indomethacine).

Physicochemical characteristics of platelet inhibitor lymphokine (LSPA) according to the invention The suppressor effect remained unchanged after dialysis of the supernatant of lymphocytes for 24 hours against a buffer solution of phosphate (PBS). The inhibitor factor was stable with respect to heat (56° C. for one hour or 100° C. for 5 minutes) and acids, since dialysis for 24 hours against a buffer at pH2 did not alter its suppressor effect, as is seen from Table 3 below which shows the physicochemical properties of LSPA: the stability of LSPA with respect to heat was evaluated by heating the supernatants on the water bath at 56° C. for 120 minutes, or at 100° C. for 5 to 10 minutes. The dialysed LSPA was prepared by dialysis of the supernatant at 4° C. for 24 hours against PBS, with multiple changes of medium. The supernatants treated with acid were prepared by dialysis at 4° C. for 24 hours against glycine buffer at pH2, followed by dialysis for 24 additional hours against PBS to remove the excess acid.

TABLE 3

| Physicochemical properties of PSPA | |
|---|---|
| Treatment | Inhibition index % |
| A. Heating | 64.0 ± 1.4 |
| 120 minutes at 56° C. | 65.7 ± 5.6 |
| 5 minutes at 100° C. | 74.8 ± 8.8 |
| B. Dialysis for 24 hours | 64.3 ± 3.6 |
| C. Acid treatment for 24 hours | 68.5 ± 2.5 |

As is shown by accompanying FIG. 6 which illustrates the percentage inhibition of the cytotoxicity of supernatants treated by various enzymes, respectively trypsin, protease K and neuraminidase, lymphokine isolated according to the present invention is sensitive to trypsin and to protease K, whilst neuraminidase has no influence on its activity.

Figure 7:
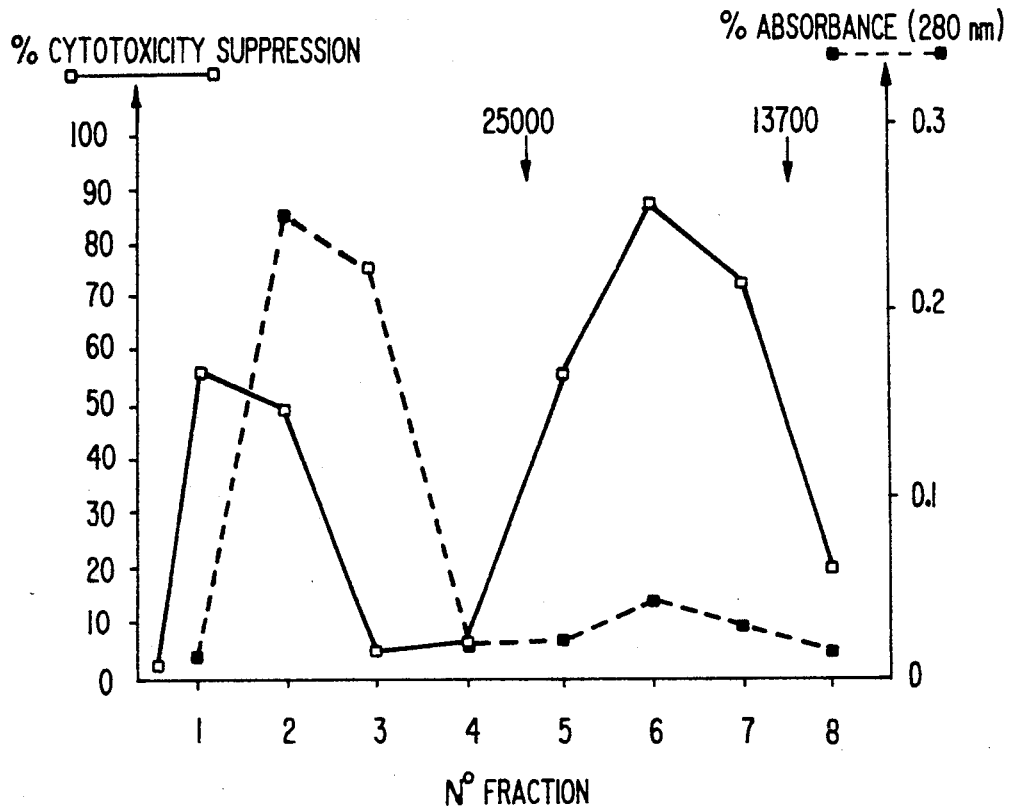
FIG. 7 shows a chromatographic profile of the inhibitor lymphokine of blood platelets according to the present invention.

A chromatographic profile of the inhibitor lymphokine of blood platelets, according to the present invention, on a molecular sieve of Sephadex-G75, is shown in FIG. 7. The LSPA was fractionnated on a Sephadex-G75 column prepared in phosphate buffer (pH 7.4). The eluted fractions were tested for their LSPA activity in anti-schistosome, IgE-dependent platelet cytotoxicity. The suppressive activity was detected in two peaks, but the optimal activity was found in the second peak, the smallest, migrating into the range of molecular weights less than or equal to 25,000 and preferably comprised between 18,000 and 20,000; the first and largest peak could correspond to an agregated form of the molecule.

Figure 8:
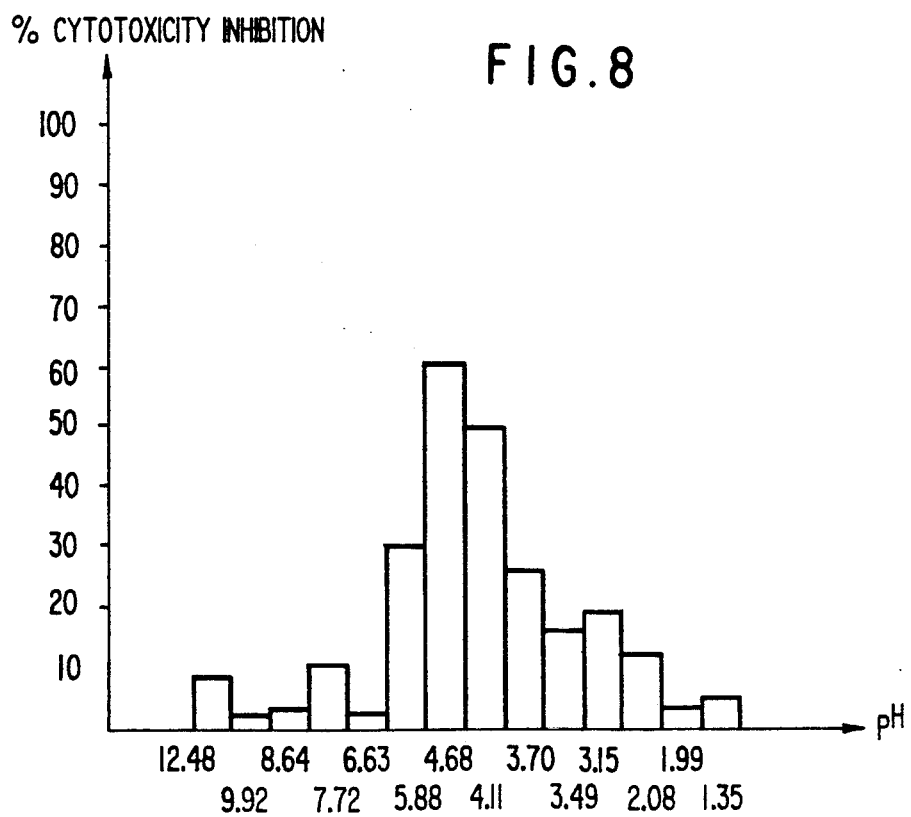
FIG. 8 shows the percentage inhibition of cytotoxicity as a function of pH.

The electric charge of the LSPA platelet inhibitor lymphokine was examined: the activity was maximum at an isoelectric point (Pi) comprised between 4.1 and 4.6, as is shown by FIG. 8 which illustrates the percentage inhibition of cytotoxicity as a function of pH. Focusing the isoelectric point of the LSPA was performed in a column of Sephadex-G75 containing 5% of support ampholines in a pH range of 3.8 to 10 for 16 hours, at a constant power of 8 watts. Each gel fraction was eluted, dialysed overnight against a PBS containing NaCl to remove the ampholines, after which its suppressor activity was examined by evaluating its IgE-dependent platelet cytotoxicity with respect to Schistosomules.

It results from the foregoing that LSPA lymphokine inhibits the effector functions of blood platelets, which suggests that it plays a role in the regulation of immunopathological disorders in which the IgE level is increased, particularly in atopic allergies, and more particularly in asthma. Through this fact, LSPA constitutes an immunopharmacological substance of great interest for the treatment of allergic disorders in which the platelets seem to be involved.

The description which follows refers to an example of the preparation of LSPA lymphokine according to the present invention, which is given by way of illustration of one of the objects of the present invention, and has no limiting character.

Example of the preparation of purified LSPA lymphokine

1. Preparation of T lymphocytes supernatants

The T lymphocyte supernatants can be obtained either by mitogenic stimulation, or by antigenic stimulation, as described below.

A. By mitogenic stimulation
from human cells 3.10⁶ peripheral or amygdal cells taken up from man, were incubated in RPMI-FCS [that is to say RPMI-1640 medium containing 5% of foetal calf serum inactivated by heat (FSC)] with Concanavaline A (0.01 at 5 μg/ml) at 37° C. in culture plates comprising cups with a flat bottom, for 24 hours, in a moist atmosphere containing 5% of $CO_2$. Cells were then washed to remove the concanavaline A and cultivated for 24 hours. The supernatants of each cup were recovered, centrifuged at 400 xg and filtered through membranes of porosity 0.22 μm, after which, if they were not used immediately, were stored at −20° C.

from murine cells 1.10 lymphocytes of lymphatic ganglions were used and the supernatants prepared as described above.

B. By antigenic stimulation stimulation of human T cells coming from a patient afflicted with Echinicoccosis was carried out in RMPI-FCS medium by the addition of crude extracts of Echinococcus granulosus (final concentration: 5,40 or 100) in the presence of irradiated (2000 rads, 2 minutes) autologous peripheral blood mononuclear cells (MCPB). After having dwelt for 24 hours in a moist atmosphere, the cells were washed to remove the aforesaid extracts and they were cultured for 4 days. The culture supernatant was recovered, filtered through a membrane of 0.22 μm and stored at −20° C. if not used immediately, the T cells obtained from lymphatic ganglions are rats infected with S. mansoni (14, 35 or 56 days of infection) were incubated in RPMI-FCS medium supplemented with IL2 (Interleukine 2), irradiated thymus cells of the rat (APC) and antigen of the S. mansoni adult worm (50 μg/ml of final concentration) in culture plates with multiple cups with a flat bottom, in a moist atmosphere containing 5% $CO_2$. This stimulation was performed every 5 days and the 15th day, the supernatants were recovered, centrifuged to eliminate therefrom all contaminated cells possibly present, and filtered through membranes of 0.22 μm, before being stored at −20° C., if necessary. At the same time, the growth response of the T cells was measured under these conditions, after a pulse of 16 hours with I μCi of H-Thymidine (1Ci/mmole), the incorporated radioactivity being determined by filtration of the culture through Millipore membranes and counting of the filters in a liquid scintillation fluid, in a beta-spectrometer.

2. Purification of supernatants to extract therefrom the active lymphokine (LSPA)

2.1 The supernatant, if necessary defrosted after storage, was dialysed in an Amicon cell (UM5 membrane) to remove therefrom the salts and the small molecules.

2.2 After dialysis, the LSPA lymphokine is purified by gel filtration on a column of extra fine Biogel P30 (granulometry 400 mesh) in a 1% AcOH medium, at a linear flow rate of 2 cm/hour. The effluents control is effected by reading at 254 nm and by researching the biological or immunological activity as described below. The fractions thus localised were combined and freeze dried.

2.3 The protein (LSPA lymphokine) is then subjected to reverse phase chromatography (HPLC) on a bonded silica gel (such as octadecylsilane, for example) whose particles are of controlled granulometry (5 um) and whose pores are calibrated (300 Å). The elution was performed by means of $CH_3CN$—$H_2O$ ranging from 1-99 to 60-40, in 3 hours. To these two phases was added 1% of trifluoroacetic acid for ionic matching.

The detection was done by optical density recording at 215 nm and determination of the biological activity. The fractions so located were then freeze dried and checked: they were constituted by LSPA lymphokine.

3. Detection of biological activity

The biological activity was detected by the aptitude of the platelets to kill schistosome larvae in the presence of specific IgEs, and by evaluation of the chemoluminescence induced by the oxidating metabolism in the presence of luminol and luciferin.

4. Determination of molecular weight of LSPA lymphokine according to the invention The supernatant stimulated by Concanavaline A, in the example described, concentrated (2 ml), was filtered through a Sephadex G-75 column (1.8×38 cm) and diluted with PBS at the flow rate of 5 ml/hour. The lymphokinic activity of each fraction was tested as described in 3. above.

To determine the molecular weight of the lymphokine, the chromatogram was calibrated with a kit for calibration of low molecular weights (supplied by PHARMACIA, UPPSALA, Sweden) containing bovine serum-albumin (BSA, m.w. 67000), of ovalbumin (m.w. 43000), chymotrysinogen A (m.w. 25000) and ribonuclease A (m.w. 13700). The molecular weight of the polypeptide which constitutes the lymphokine, determined as indicated above, was comprised between 15000 and 20000.

Thus as emerges from the foregoing there was isolated, according to the present invention, a lymphokine which is distinguished from lymphokines identified until now, both by its biological properties and by its physico-chemical properties, and which inhibits the effector functions of platelets, thus providing an immunopharmacological substance adapted to play an important role in the regulation of immunopathological disorders in which the IgE level is increased, and more particularly in atopic allergies and more especially still in asthma.

We claim:

1. An essentially pure lymphokine, wherein said lymphokine:
   a) is obtained from the supernatant of T OKT8+ lymphocyte cultures after mitogenic or antigenic stimulation;
   b) inhibits IgE-dependent platelet cytotoxicity with respect to young larva of Schistosomia mansoni;
   c) inhibits platelet activation in non-IgE dependent intolerances;
   d) has a molecular weight in the range of about 15-20 kDa; and
   e) has a pI of about 3.7-5.0.

2. The lymphokine of claim 1, wherein said lymphokine is obtained from the supernatant of T OKT8+ lymphocyte culture which have been stimulated by a mitogen or an antigen.

3. The lymphokine of claim 2, wherein said stimulating antigen is selected from the group consisting of antigens of Echinococcus granulosus and antigens of Schistosomia mansoni.

4. The lymphokine of claim 1, wherein said lymphokine has a pI of about 3.70-4.68.

5. The lymphokine of claim 1, wherein said lymphokine has a pI of 4.1-4.6.

6. The lymphokine of claim 1, wherein said lymphokine is stable to heating at 56° C. for 1 hour or 100° C. for 5 minutes.

7. The lymphokine of claim 1, wherein said lymphokine is stable to dialysis at 4° C. for 24 hours at pH=2.

8. The lymphokine of claim 1, wherein the inhibitory activity of said lymphokine is stable to treatment with neuraminidase, and said inhibitory activity is decreased by treatment with trypsin and protease K.

9. The lymphokine of claim 1, where in said lymphokine adsorbs to the surface of platelets.

10. A process for the preparation of the lymphokine of claim 1, comprising the steps of:
   a) stimulating and cultivating T-cells comprising OKT8+ lymphocytes with a mitogen or with an antigen selected from the group consisting of antigens of Echinococcus granulosus and antigens of Schistosomia mansoni;
   b) recovering the culture supernatants, clarifying the supernatants by centrifugation and filtration through a membrane having a pore dimension of about 0.22 $\mu$m;
   c) fractionating the filtrate from said membrane by gel filtration on a molecular sieve; and
   d) recovering the fractions from said molecular sieve which inhibit platelet activation,
   e) submitting recovered fractions from step d) to reverse phase chromatography on a bonded silica gel of 5 $\mu$m particle size and a pore diameter of about 300 angstroms and eluted during about 3 hours with a $CH_3CN$—$H_2O$ eluate gradient, ranging from a ratio of 1/99 to 60/40, said eluate containing 1% trifluoroacetic acid, and recovering the fractions from said chromatography which inhibit platelet activation.

* * * * *